United States Patent
Yang et al.

(10) Patent No.: US 9,909,984 B2
(45) Date of Patent: Mar. 6, 2018

(54) MULTICHANNEL LABEL-FREE BIOSENSING OPTICAL-FIBER SYSTEM

(71) Applicant: Tian Yang, Shanghai (CN)

(72) Inventors: Tian Yang, Shanghai (CN); Xiaolong He, Shanghai (CN)

(73) Assignee: Tian Yang, Minhang District, Shanghai (CN)

( * ) Notice: Subject to any disclaimer, the term of this patent is extended or adjusted under 35 U.S.C. 154(b) by 0 days.

(21) Appl. No.: 15/019,974

(22) Filed: Feb. 10, 2016

(65) Prior Publication Data

US 2017/0227460 A1    Aug. 10, 2017

(51) Int. Cl.

| | |
|---|---|
| *G01N 21/49* | (2006.01) |
| *G02B 6/28* | (2006.01) |
| *G01N 33/487* | (2006.01) |
| *G02B 6/26* | (2006.01) |
| *G01N 33/497* | (2006.01) |

(52) U.S. Cl.
CPC ........... *G01N 21/49* (2013.01); *G01N 33/487* (2013.01); *G01N 33/497* (2013.01); *G02B 6/262* (2013.01); *G02B 6/2808* (2013.01); *G01N 2201/0621* (2013.01); *G01N 2201/0683* (2013.01); *G01N 2201/06113* (2013.01); *G01N 2201/0846* (2013.01)

(58) Field of Classification Search
None
See application file for complete search history.

(56) References Cited

U.S. PATENT DOCUMENTS 8,617,470 B2 *  12/2013  Dave ..................... G01N 21/45
                                                                422/500

* cited by examiner

*Primary Examiner* — Jerry Rahll
(74) *Attorney, Agent, or Firm* — Global IP Services; Tianhua Gu (57) ABSTRACT

The present invention provides a multichannel label-free biosensing fiber-optic system, which comprises one or more light sources coupled into optical fibers, one or more optical fiber circuits for performing coupling or/and directional transmission of optical-fiber guided lightwaves, one or more optical-fiber-input and optical-fiber-output optical switches, a plurality of optical fibers provided with label-free optical sensing elements working in the reflection manner on the optical fiber ends, and the light detection parts, wherein the optical-fiber-input and optical-fiber-output optical switch is provided with a plurality of outputs and/or a plurality of inputs, and with the plurality of outputs and/or plurality of inputs, by the switching function, the reflected light from the label-free optical sensing elements working in the reflection manner on the designated optical fiber ends is received by the light detection part, so that multichannel sensing is realized.

19 Claims, 3 Drawing Sheets

MULTICHANNEL LABEL-FREE BIOSENSING OPTICAL-FIBER SYSTEM

BACKGROUND OF THE PRESENT INVENTION

Field of the Invention

The present invention belongs to the field of biosensing and instrument design, and in particular relates to a multichannel label-free biosensing fiber-optic system.

Description of Related Arts

Quantitative measurement of the interaction between biological molecules is widely employed in life science basic research, new drug screening and development, and food industry. Traditionally, the enzyme-linked immunosorbent assay technology is used for such detection and analysis. In recent years, the label-free optical biosensing technology which does not need fluorescence labeling has a rapid development. The label-free sensing technology has the advantages that the natural characteristics of samples are maintained, and the time and labor of operators are greatly saved; more importantly, the label-free sensing technology can be used for real-time measurement of the kinetic process of the interaction between molecules, which has a great value for scientific research and drug screening.

In a label-free optical biosensing system in which light transmission is mostly via free space, in order to realize parallel detection (multichannel sensing) of a plurality of samples or reaction processes, usually a plurality of light detection parts need to be used and thereby the system volume and cost are increased. By using optical fibers as the transmission media and introducing the optical signal processing technologies in fiber-optic communication into the biosensing system, the system performance can be considerably improved. However, reported label-free biosensing fiber-optic systems lack good compatibility with fiber-optic communication technologies, so that for realization of multichannel sensing, either a transmission detection framework is used which is difficult to operate, or it still partially depends on free-space light transmission.

SUMMARY OF THE PRESENT INVENTION

In view of the disadvantages of the prior art, the purpose of the present invention is to provide a multichannel label-free biosensing fiber-optic system, so as to realize a system which uses optical fiber circuits, label-free sensing elements working in the reflection manner on the optical fiber ends, and optical switches as core components, and which is used for performing multichannel parallel sensing of biochemical samples.

In order to realize the above-mentioned and other related purposes, the present invention provides a multichannel label-free biosensing fiber-optic system, which comprises one or more light sources coupled into optical fibers, one or more optical fiber circuits for performing coupling or/and directional transmission of optical-fiber guided lightwaves, one or more optical-fiber-input and optical-fiber-output optical switches, a plurality of optical fibers provided with label-free optical sensing elements working in the reflection manner on the optical fiber ends, and the light detection parts, wherein the label-free optical sensing elements working in the reflection manner are attached to the ends of the optical fibers, but not separated from the optical fibers, the label-free optical sensing element working in the reflection manner reflects the optical fiber guided waves, which have come from the light source, passed through the optical fiber circuit and been incident upon it, back to the same optical fiber it is attached to, the reflected light passes through the optical fiber circuit and then is received and measured by the light detection part, the optical-fiber-input and optical-fiber-output optical switch is provided with a plurality of outputs and/or a plurality of inputs, and with the plurality of outputs and/or plurality of inputs, by the switching function, the reflected light from the label-free optical sensing elements working in the reflection manner on the designated optical fiber ends is received by the light detection part, so that multichannel sensing is realized.

During measurement, the label-free optical sensing elements working in the reflection manner are immersed in the samples to be detected, the label-free optical sensing element working in the reflection manner reflects the optical fiber guided waves, which have come from the light source, passed through the optical fiber circuit and been incident upon it, back to the same optical fiber it is attached to, the reflected light passes through the optical fiber circuit and then is received and measured by the light detection part. The measurement results reveal the information of the samples to be detected, wherein by operating the optical-fiber-input and optical-fiber-output optical switch, the reflected light coming from different label-free optical sensing elements working in the reflection manner at different moments can be received by the light detection part, so that multichannel sensing is realized.

As a preferred solution of the multichannel label-free biosensing fiber-optic system provided by the present invention, the optical fiber circuit comprises one or more directional coupling devices, which is used for performing coupling and directional transmission of optical-fiber guided lightwaves.

As a preferred solution of the multichannel label-free biosensing fiber-optic system provided by the present invention, the directional coupling device comprises one or a combination of directional couplers and optical circulators.

Further, the directional coupler is a 2×2 directional coupler with an optical power splitting ratio of 50%:50%.

As a preferred solution of the multichannel label-free biosensing fiber-optic system provided by the present invention, a first port of the directional coupling device is connected with the light source, a second port of the directional coupling device, which is directly and optically connected to the input of the first port of the directional coupling device, is connected with an input port of the optical-fiber-input and optical-fiber-output optical switch, the plurality of optical fibers provided with the label-free optical sensing elements working in the reflection manner on the optical fiber ends are connected with the output ports of the optical-fiber-input and optical-fiber-output optical switch, and a third port of the directional coupling device which is directly and optically connected to the input of the second port of the directional coupling device, is connected with the light detection part.

As a preferred solution of the multichannel label-free biosensing fiber-optic system provided by the present invention, the optical fiber circuit further comprises one or more beam splitters, which is used for performing beam splitting to the optical-fiber guided lightwaves.

Further, an input port of the beam splitter is connected with the light source, each output port of the beam splitter is connected with a first port of each directional coupling device, the plurality of optical fibers provided with the label-free optical sensing elements working in the reflection manner on the optical fiber ends are respectively connected with a second port of each directional coupling device which is directly and optically connected to the input of the first port of the directional coupling device, a plurality of input ports of the optical-fiber-input and optical-fiber-output optical switch are respectively connected with a third port of each directional coupling device which is directly and optically connected to the input of the second port of the directional coupling device, and an output port of the optical-fiber-input and optical-fiber-output optical switch is connected with the light detection part.

As a preferred solution of the multichannel label-free biosensing fiber-optic system provided by the present invention, the optical fiber circuit further comprises one or more beam combiners, which is used for performing beam combining to the optical-fiber guided lightwaves in the plurality of optical fibers.

Further, an input port of the optical-fiber-input and optical-fiber-output optical switch is connected with the light source, a plurality of output ports of the optical-fiber-input and optical-fiber-output optical switch are respectively connected with a first port of each directional coupling device, the plurality of optical fibers provided with the label-free optical sensing elements working in the reflection manner on the optical fiber ends are respectively connected with a second port of each directional coupling device which is directly and optically connected to the input of the first port of the directional coupling device, a plurality of input ports of the beam combiner are respectively connected with a third port of each directional coupling device which is directly and optically connected to the input of the second port of the directional coupling device, and an output port of the beam combiner is connected with the light detection part.

As a preferred solution of the multichannel label-free biosensing fiber-optic system provided by the present invention, the multichannel label-free biosensing fiber-optic system comprises more than one light sources coupled into optical fibers, or/and more than one optical-fiber-input and optical-fiber-output optical switches, or/and more than one light detection parts, or/and more than one directional coupling devices, or/and more than one beam splitters, or/and more than one beam combiners.

As a preferred solution of the multichannel label-free biosensing fiber-optic system provided by the present invention, the light source comprises one or a combination of halogen lamps, light emitting diodes, super-luminescent diodes, super-continuum sources, amplified spontaneous emission sources and lasers.

As a preferred solution of the multichannel label-free biosensing fiber-optic system provided by the present invention, the light detection part comprises one or a combination of spectrometers and optical power detectors.

As a preferred solution of the multichannel label-free biosensing fiber-optic system provided by the present invention, the label-free optical sensing elements working in the reflection manner are fabricated on the end facets of the optical fibers or/and are bonded to the end facets of the optical fibers.

Further, the label-free optical sensing elements working in the reflection manner are gold films which are fabricated on the end facets of the optical fibers or/and are bonded to the end facets of the optical fibers and which are provided with nano-slit arrays.

As a preferred solution of the multichannel label-free biosensing fiber-optic system provided by the present invention, the optical fibers in the multichannel label-free biosensing fiber-optic system, corresponding to the lightwaves transmitted thereby, are single-mode optical fibers or polarization-maintaining optical fibers, or a combination of single-mode optical fibers and polarization-maintaining optical fibers.

As a preferred solution of the multichannel label-free biosensing fiber-optic system provided by the present invention, the optical fibers in the multichannel label-free biosensing fiber-optic system, corresponding to the lightwaves transmitted thereby, are multi-mode optical fibers, or a combination of single-mode optical fibers and multi-mode optical fibers, or a combination of polarization-maintaining optical fibers and multi-mode optical fibers, or a combination of single-mode optical fibers, polarization-maintaining optical fibers and multi-mode optical fibers.

Further, a diameter range of the wave guiding fiber cores of the multi-mode optical fibers is 1 μm-10 mm.

Further, the diameter range of the wave guiding fiber cores of the multi-mode optical fibers is 1 μm-200 μm.

Further, the diameter range of the wave guiding fiber cores of the multi-mode optical fibers is 1 μm-100 μm.

As a preferred solution of the multichannel label-free biosensing fiber-optic system provided by the present invention, the samples to be detected with the multichannel label-free biosensing fiber-optic system are substances that can induce optical refractive index or/and optical path length change, comprising biological molecules, or/and chemical molecules or/and metal ions.

Further, the samples to be detected are solution containing molecules to be detected, and when the molecules to be detected adhere to the label-free optical sensing elements working in the reflection manner, the spectrum or/and intensity of reflected light changes and is measured.

As described above, the present invention provides a multichannel label-free biosensing fiber-optic system, which comprises one or more light sources coupled into optical fibers, one or more optical fiber circuits for performing coupling or/and directional transmission of optical-fiber guided lightwaves, one or more optical-fiber-input and optical-fiber-output optical switches, a plurality of optical fibers provided with label-free optical sensing elements working in the reflection manner on the optical fiber ends, and the light detection parts, wherein the label-free optical sensing elements working in the reflection manner are attached to the ends of the optical fibers, but not separated from the optical fibers, the label-free optical sensing element working in the reflection manner reflects the optical fiber guided waves, which have come from the light source, passed through the optical fiber circuit and been incident upon it, back to the same optical fiber it is attached to, the reflected light passes through the optical fiber circuit and then is received and measured by the light detection part, the optical-fiber-input and optical-fiber-output optical switch is provided with a plurality of outputs and/or a plurality of inputs, and with the plurality of outputs and/or plurality of inputs, by the switching function, the reflected light from the label-free optical sensing elements working in the reflection manner on the designated optical fiber ends is received by the light detection part, so that multichannel sensing is realized. The present invention provides a label-free biosensing fiber-optic system with parallel multi-channels for detecting a plurality of biological samples. Thanks to utilization of fiber-optic communication technologies such as optical fiber circuit and optical switch, the system can comprise just one light detection part, thereby the complexity of the system is greatly lowered, the size is reduced and the stability is good.

DESCRIPTION OF COMPONENT MARK NUMBERS

10 Light source
11 Directional coupling device
12 Optical-fiber-input and optical-fiber-output optical switch
13 Optical fiber provided with label-free optical sensing element working in the reflection manner on the optical fiber end
131 Label-free optical sensing element working in the reflection manner
14 Light detection part
15 Beam splitter
16 Beam combiner
17 Sample to be detected

DETAILED DESCRIPTION OF THE PREFERRED EMBODIMENTS

The implementation mode of the present invention will be described below through specific embodiments. One skilled in the art can easily understand other advantages and effects of the present invention according to contents disclosed by the description. The present invention can also be implemented or applied through other different specific implementation modes. Various modifications or changes can also be made to all details in the description based on different points of view and applications without departing from the spirit of the present invention.

Please refer to FIGS. 1-6. It needs to be stated that the drawings provided in the following embodiments are just used for schematically describing the basic concept of the present invention, thus only illustrate components only related to the present invention and are not drawn according to the numbers, shapes and sizes of components during actual implementation, the configuration, number and scale of each component during actual implementation thereof may be freely changed, and the component layout configuration thereof may be more complex.

Embodiment 1

Figure 1:
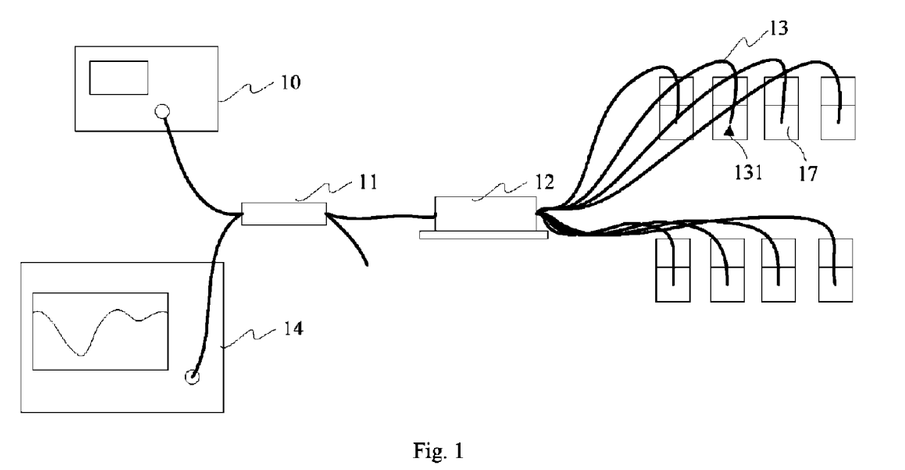
FIG. 1 illustrates a structural schematic diagram of a multichannel label-free biosensing fiber-optic system according to embodiment 1 of the present invention.
Figure 5:
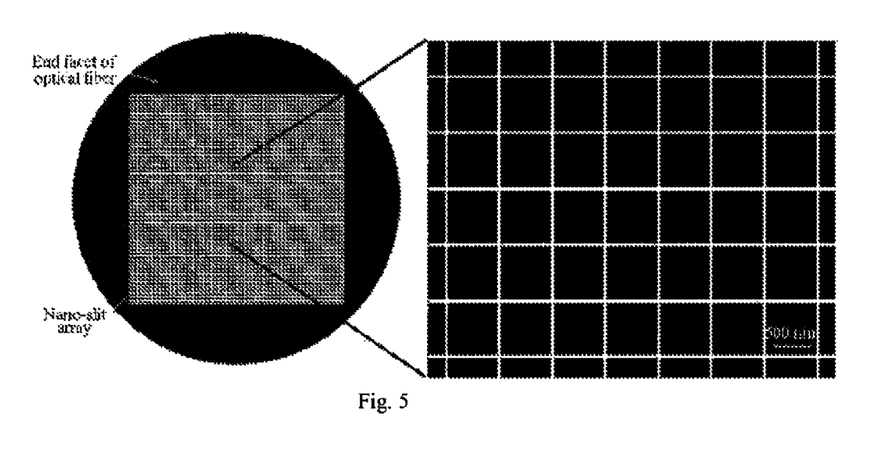
FIG. 5 illustrates a structural schematic diagram of a label-free optical sensing element working in the reflection manner in the multichannel label-free biosensing fiber-optic system according to the present invention.

As shown in FIGS. 1 and 5, this embodiment provides a multichannel label-free biosensing fiber-optic system, which comprises a light source 10 coupled into an optical fiber, an optical fiber circuit for performing coupling and directional transmission of optical-fiber guided lightwaves, an optical-fiber-input and optical-fiber-output optical switch 12, a plurality of optical fibers 13 provided with label-free optical sensing elements working in the reflection manner 131 on the optical fiber ends, and a light detection part 14, wherein the label-free optical sensing elements working in the reflection manner 131 are attached to the ends of the optical fibers 13, but not separated from the optical fibers, the label-free optical sensing element working in the reflection manner 131 reflects the optical fiber guided waves, which have come from the light source 10, passed through the optical fiber circuit and been incident upon it, back to the same optical fiber it is attached to, the reflected light passes through the optical fiber circuit and then is received and measured by the light detection part 14, the optical-fiber-input and optical-fiber-output optical switch 12 is provided with a plurality of outputs, and with the plurality of outputs, by the switching function, the reflected light from the label-free optical sensing elements working in the reflection manner 131 on the designated optical fiber ends is received by the light detection part 14, so that multichannel sensing is realized.

During measurement, the label-free optical sensing elements working in the reflection manner 131 are immersed in the samples to be detected 17, the label-free optical sensing element working in the reflection manner 131 reflects the optical fiber guided waves, which have come from the light source 10, passed through the optical fiber circuit and been incident upon it, back to the same optical fiber it is attached to, the reflected light passes through the optical fiber circuit and then is received and measured by the light detection part 14. The measurement results reveal the information of the samples to be detected 17, wherein by operating the optical-fiber-input and optical-fiber-output optical switch 12, the reflected light coming from different label-free optical sensing elements working in the reflection manner 131 at different moments can be received by the light detection part 14, so that multichannel sensing is realized.

In this embodiment, the optical fibers in the multichannel label-free biosensing fiber-optic system are single-mode optical fibers corresponding to the lightwaves transmitted thereby. By using the single-mode optical fibers, the compatibility of the system with the optical communication technologies can be improved.

As shown in FIG. 1, the optical fiber circuit comprises a directional coupling device 11, which is used for performing coupling and directional transmission of optical-fiber guided lightwaves. In this embodiment, the directional coupling device 11 is a 2×2 directional coupler with an optical power splitting ratio of 50%:50%. A first port of the 2×2 directional coupler is connected with the light source 10, a second port of the directional coupling device 11, which is directly and optically connected to the input of the first port of the directional coupling device 11, is connected with an input port of the optical-fiber-input and optical-fiber-output optical switch 12, and the plurality of optical fibers 13 provided with the label-free optical sensing elements working in the reflection manner 131 on the optical fiber ends are connected with the output ports of the optical-fiber-input and optical-fiber-output optical switch 12. A third port of the directional coupling device, which is directly and optically connected to the input of the second port of the directional coupling device, is connected with the light detection part 14.

As shown in FIG. 5, the label-free optical sensing elements working in the reflection manner 131 are glued to the end facets of the optical fibers, the label-free optical sensing elements working in the reflection manner are gold films which are provided with nano-slit arrays, the thickness of the gold films is 25 nm, the nano-slits penetrate through the entire thickness of the gold films, the period of the nano-slits is 635 nm and the width of the nano-slits is 50 nm. Of course, the label-free optical sensing elements working in the reflection manner 131 can be either first fabricated and then bonded to the end facets of the optical fibers through a gluing method as that in this embodiment, or be directly fabricated on the end facets of the optical fibers through methods such as electron beam lithography and focused ion beam milling. In addition, the label-free optical sensing elements working in the reflection manner which are realized by other methods are also applicable to the present invention and are not limited to the examples listed here.

As shown in FIG. 1, specifically, a broad-band light source (such as a halogen lamp, a light emitting diode, a super-luminescent diode, a supercontinuum source or an amplified spontaneous emission source) is coupled into a single-mode optical fiber, then lightwaves enter a first port of a single-mode optical-fiber-input and single-mode optical-fiber-output 2×2 directional coupler and are divided into two paths, wherein one path is directionally coupled and output to a second port of the directional coupler and then is transmitted by the optical fiber to enter an input port of a single-mode optical-fiber-input and single-mode optical-fiber-output 1×N optical switch (such as a 1×8 mechanical optical switch), i.e., the "1" port, and by the switching function the lightwaves output out of one designated port of the "N" output ports. Then, after being transmitted by the optical fiber, the lightwaves enter an optical fiber 13 provided with a label-free optical sensing element working in the reflection manner 131 on the optical fiber end, and subsequently the label-free optical sensing element working in the reflection manner 131 reflects the incident optical fiber guided waves back to the same optical fiber it is attached to. The label-free optical sensing element working in the reflection manner 131 is immersed in a sample to be detected 17. With behaviors such as association, dissociation and concentration change of a substance to be detected in the sample, the spectrum and intensity of the reflected light change correspondingly. The reflected light enters the same designated output port of the 1×N optical switch through the optical fiber in the reverse direction and comes out of the input port thereof. Then, the lightwaves are input into the second port of the 2×2 directional coupler and then are divided into two paths, wherein one path is directionally coupled and output to a third port of the directional coupler. Finally, the lightwaves are transmitted by the optical fiber and then are received and measured by the light detection part 14. In this embodiment, the light detection part 14 is a spectrometer (such as a grating spectrometer). The spectrometer measures the spectrum of the reflected light and thereby infers the conditions of the sample to be detected 17. In this system, by operating the optical switch to designate a different port of its N output ports at different time moments, the reflected light coming from different label-free optical sensing elements working in the reflection manner 131 can be received by the light detection part 14 at different time moments to realize the multichannel parallel sensing of N samples.

Of course, in the above-mentioned solution, the light source can also be a single-wavelength laser, correspondingly what is measured by the light detection part 14 is the intensity of the reflected light, for example, the light detection part 14 is an optical power detector and it comprises a photodiode.

In addition, it needs to be mentioned that, firstly, the samples to be detected 17 can be liquid or gas; secondly, the substance to be detected are the substance that can induce optical refractive index or optical path length changes, which can be biological molecules, chemical molecules, metal ions and the like; more specifically, the samples to be detected are solutions containing certain molecules to be detected; when such molecules adhere to the label-free optical sensing elements working in the reflection manner, the spectrum or the intensity of the reflected light changes and is measured; and thirdly, the positions of the samples to be detected can be in micro-fluids, microtiter plates or other common containers.

Embodiment 2

Figure 2:
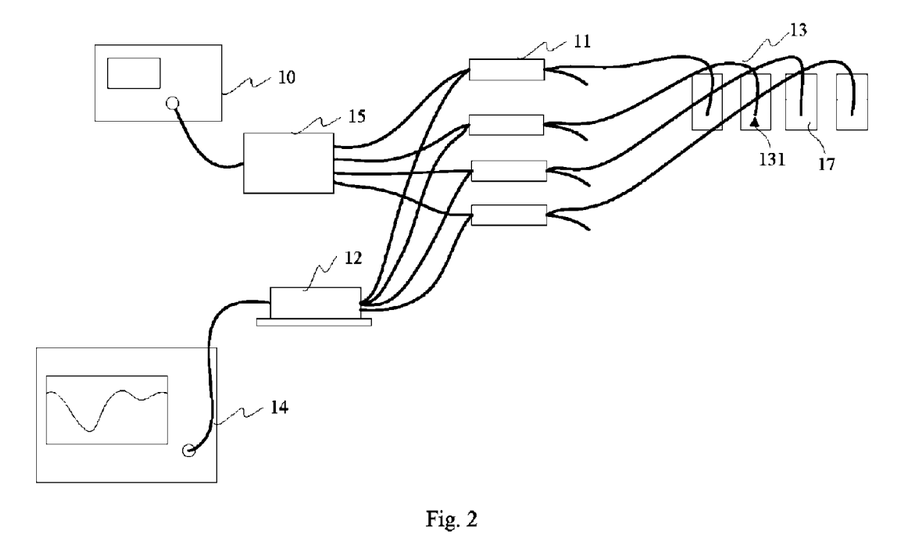
FIG. 2 illustrates a structural schematic diagram of a multichannel label-free biosensing fiber-optic system according to embodiment 2 of the present invention.

As shown in FIG. 2, this embodiment provides a multichannel label-free biosensing fiber-optic system, which comprises a light source 10 coupled into an optical fiber, an optical fiber circuit for performing coupling and directional transmission of optical-fiber guided lightwaves, an optical-fiber-input and optical-fiber-output optical switch 12, a plurality of optical fibers 13 provided with label-free optical sensing elements working in the reflection manner 131 on the optical fiber ends, and a light detection part 14, wherein the label-free optical sensing elements working in the reflection manner 131 are attached to the ends of the optical fibers 13, but not separated from the optical fibers, the label-free optical sensing element working in the reflection manner 131 reflects the optical fiber guided waves, which have come from the light source 10, passed through the optical fiber circuit and been incident upon it, back to the same optical fiber it is attached to, the reflected light passes through the optical fiber circuit and then is received and measured by the light detection part 14, the optical-fiber-input and optical-fiber-output optical switch 12 is provided with a plurality of inputs, and with the plurality of inputs, by the switching function, the reflected light from the label-free optical sensing elements working in the reflection manner 131 on the designated optical fiber ends is received by the light detection part 14, so that multichannel sensing is realized.

During measurement, the label-free optical sensing elements working in the reflection manner 131 are immersed in the samples to be detected 17, the label-free optical sensing element working in the reflection manner 131 reflects the optical fiber guided waves, which have come from the light source 10, passed through the optical fiber circuit and been incident upon it, back to the same optical fiber it is attached to, the reflected light passes through the optical fiber circuit and then is received and measured by the light detection part 14. The measurement results reveal the information of the samples to be detected 17, wherein by operating the optical-fiber-input and optical-fiber-output optical switch 12, the reflected light coming from different label-free optical sensing elements working in the reflection manner 131 at different moments can be received by the light detection part 14, so that multichannel sensing is realized.

In this embodiment, the optical fibers in the multichannel label-free biosensing fiber-optic system are single-mode optical fibers corresponding to the lightwaves transmitted thereby. By using the single-mode optical fibers, the compatibility of the system with the optical communication technologies can be improved.

As shown in FIG. 2, the optical fiber circuit comprises directional coupling devices 11, which are used for performing coupling and directional transmission of optical-fiber guided lightwaves. In this embodiment, each directional coupling device 11 is a 2×2 directional coupler with an optical power splitting ratio of 50%:50%. The optical fiber circuit further comprises a beam splitter 15, which is used for performing beam splitting to the optical-fiber guided lightwaves. An input port of the beam splitter is connected with the light source, each output port of the beam splitter is connected with a first port of each 2×2 directional coupler, and second ports of the 2×2 directional couplers, which are directly and optically connected to the inputs of the first ports of the 2×2 directional couplers, are respectively connected with the plurality of optical fibers 13 provided with the label-free optical sensing elements working in the reflection manner 131 on the optical fiber ends. A plurality of input ports of the optical-fiber-input and optical-fiber-output optical switch 12 are respectively connected with a third port of each 2×2 directional coupler, which is directly and optically connected to the input of the second port of each 2×2 directional coupler, and an output port of the optical-fiber-input and optical-fiber-output optical switch 12 is connected with the light detection part 14.

As shown in FIG. 2, specifically, lightwaves coming from a light source are coupled to an optical fiber and firstly are divided into N paths by a beam splitter 15. The N paths of lightwaves respectively enter a first port of a 2×2 directional coupler and are each divided into two paths, wherein one path is directionally coupled and output to a second port of the directional coupler and then is transmitted by the optical fiber to enter an optical fiber 13 provided with a label-free optical sensing element working in the reflection manner 131 on the optical fiber end, and subsequently the label-free optical sensing element working in the reflection manner 131 reflects the incident optical fiber guided waves back to the same optical fiber it is attached to. Then, the lightwaves enter the second port of the 2×2 directional coupler and are then divided into two paths, wherein one path is directionally coupled and output to a third port of the directional coupler. The lightwaves are then transmitted by the optical fiber to enter an input port of an N×1 optical switch, i.e., one of the "N" ports, and then by the switching function the lightwaves from one designated port of the N input ports are output out of an output port thereof. Finally, the lightwaves are transmitted by the optical fiber and then are received and measured by the light detection part 14. In this system, by operating the optical switch to designate a different port of its N input ports at different time moments, the reflected light coming from different label-free optical sensing elements working in the reflection manner 131 can be received by the light detection part 14 at different time moments to realize the multichannel parallel sensing of N samples.

Embodiment 3

Figure 3:
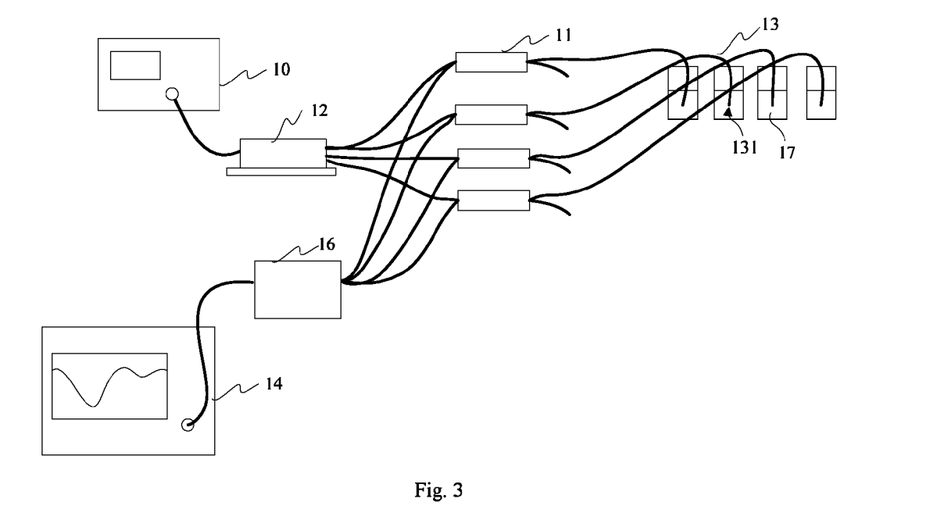
FIG. 3 illustrates a structural schematic diagram of a multichannel label-free biosensing fiber-optic system according to embodiment 3 of the present invention.

As shown in FIG. 3, this embodiment provides a multichannel label-free biosensing fiber-optic system, which comprises a light source 10 coupled into an optical fiber, an optical fiber circuit for performing coupling and directional transmission of optical-fiber guided lightwaves, an optical-fiber-input and optical-fiber-output optical switch 12, a plurality of optical fibers 13 provided with label-free optical sensing elements working in the reflection manner 131 on the optical fiber ends, and a light detection part 14, wherein the label-free optical sensing elements working in the reflection manner 131 are attached to the ends of the optical fibers 13, but not separated from the optical fibers, the label-free optical sensing element working in the reflection manner 131 reflects the optical fiber guided waves, which have come from the light source 10, passed through the optical fiber circuit and been incident upon it, back to the same optical fiber it is attached to, the reflected light passes through the optical fiber circuit and then is received and measured by the light detection part 14, the optical-fiber-input and optical-fiber-output optical switch 12 is provided with a plurality of outputs, with the plurality of outputs, by the switching function, the reflected light from the label-free optical sensing elements working in the reflection manner 131 on the designated optical fiber ends is received by the light detection part 14, so that multichannel sensing is realized.

During measurement, the label-free optical sensing elements working in the reflection manner 131 are immersed in the samples to be detected 17, the label-free optical sensing element working in the reflection manner 131 reflects the optical fiber guided waves, which have come from the light source 10, passed through the optical fiber circuit and been incident upon it, back to the same optical fiber it is attached to, the reflected light passes through the optical fiber circuit and then is received and measured by the light detection part 14. The measurement results reveal the information of the samples to be detected 17, wherein by operating the optical-fiber-input and optical-fiber-output optical switch 12, the reflected light coming from different label-free optical sensing elements working in the reflection manner 131 at different moments can be received by the light detection part 14, so that multichannel sensing is realized.

In this embodiment, the optical fibers in the multichannel label-free biosensing fiber-optic system are single-mode optical fibers corresponding to the lightwaves transmitted thereby. By using the single-mode optical fibers, the compatibility of the system with the optical communication technologies can be improved.

As shown in FIG. 3, the optical fiber circuit comprises directional coupling devices 11, which are used for performing coupling and directional transmission of the optical-fiber guided lightwaves. In this embodiment, each directional coupling device 11 is a 2×2 directional coupler with an optical power splitting ratio of 50%:50%. The optical fiber circuit further comprises a beam combiner 16, which is used for performing beam combining to the optical-fiber guided lightwaves in the plurality of optical fibers. An input port of the optical-fiber-input and optical-fiber-output optical switch 12 is connected with the light source, a plurality of output ports of the optical-fiber-input and optical-fiber-output optical switch are respectively connected with first ports of the 2×2 directional couplers, and second ports of the 2×2 directional couplers, which are directly and optically connected with the inputs of the first ports of the 2×2 directional couplers are respectively connected with the plurality of optical fibers 13 provided with the label-free optical sensing elements working in the reflection manner 131 on the optical fiber ends. A plurality of input ports of the beam combiner are respectively connected with third ports of the 2×2 directional couplers, which are directly and optically connected to the inputs of the second ports of the 2×2 directional couplers, and an output port of the beam combiner is connected with the light detection part 14.

As shown in FIG. 3, specifically, lightwaves which have come from a light source are coupled into an optical fiber, then enter an input port of an optical-fiber-input and optical-fiber-output 1×N optical switch and are designated to be output to one of N output ports by the optical-fiber-input and optical-fiber-output 1×N optical switch. Then, the lightwaves enter a first port of a 2×2 directional coupler and are divided into two paths, wherein one path is directionally coupled and output to a second port of the directional coupler and then is transmitted by the optical fiber to enter an optical fiber 13 provided with a label-free optical sensing element working in the reflection manner 131 on the optical fiber end, and subsequently the label-free optical sensing element working in the reflection manner 131 reflects the incident optical fiber guided waves back to the same optical fiber. Then, the lightwaves enter the second port of the 2×2 directional coupler and are then divided into two paths, wherein one path is directionally coupled and output to a third port of the directional coupler. The lightwaves are then transmitted by the optical fiber to enter one of the plurality of input ports of a beam combiner 16, i.e., enter the side of the beam combiner that has a plurality of optical fibers, and are output out of an output port of the beam combiner. Finally, the lightwaves are transmitted by the optical fiber and then are received and measured by the light detection part 14. In this system, by operating the optical switch to designate a different port of its N output ports at different time moments, the reflected light coming from different label-free optical sensing elements working in the reflection manner 131 can be received by the light detection part 14 at different time moments to realize the multichannel parallel sensing of N samples.

Embodiment 4

This embodiment provides a multichannel label-free biosensing fiber-optic system, the basic structure of which is as shown in embodiment 1, embodiment 2 or/and embodiment 3, wherein a more complex fiber-optic system can be realized through combining light sources 10 coupled into optical fibers, optical fiber circuits for performing coupling and directional transmission of optical-fiber guided lightwaves, optical-fiber-input and optical-fiber-output optical switches 12, a plurality of optical fibers 13 provided with label-free optical sensing elements working in the reflection manner 131 on the optical fiber ends, and light detection parts 14. For example, by using more than one light sources 10 coupled into optical fibers, or/and more than one light detection parts 14, or/and more than one beam splitters 15, or/and more than one beam combiners 16, a larger-scale parallel sensing system can be obtained. For another example, by using more than one optical-fiber-input and optical-fiber-output optical switches 12, or by changing the number of input or/and output ports of the directional coupling devices 11 or/and the optical-fiber-input and optical-fiber-output optical switches 12, parallel sensing systems with different system frameworks can be obtained.

Figure 4:
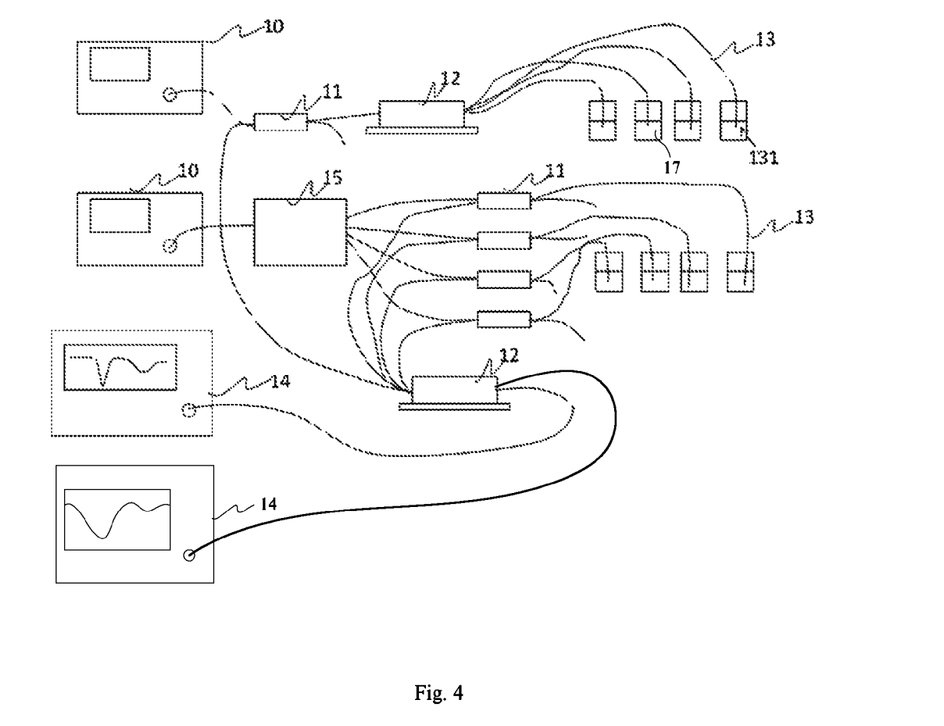
FIG. 4 illustrates a structural schematic diagram of a multichannel label-free biosensing fiber-optic system according to embodiment 4 of the present invention.

Specifically, as shown in FIG. 4, this embodiment provides a multichannel label-free biosensing fiber-optic system, which comprises two light sources 10 coupled into optical fibers, two optical-fiber-input and optical-fiber-output optical switches 12, a beam splitter 15, a plurality of directional couplers 11, a plurality of optical fibers 13 provided with label-free optical sensing elements working in the reflection manner 131 on the optical fiber ends, and two light detection parts 14, the connections between the above-mentioned components can be clearly obtained according to the description of embodiment 1, embodiment 2 and FIG. 4 and thereby are not described one by one again. The two optical-fiber-input and optical-fiber-output optical switches 12 are respectively an optical-fiber-input and optical-fiber-output 1×N optical switch and an optical-fiber-input and optical-fiber-output M×2 optical switch, wherein the two output ports of the optical-fiber-input and optical-fiber-output M×2 optical switch are respectively connected with a light detection part.

Embodiment 5

This embodiment provides a multichannel label-free biosensing fiber-optic system, the basic structure of which is as shown in embodiment 1, embodiment 2, embodiment 3 or/and embodiment 4, wherein the 2×2 directional couplers in embodiment 1, embodiment 2, embodiment 3 or/and embodiment 4 are replaced by three-port optical circulators. In each optical circulator, light input from the first (second, third) port is output out of the second (third, first) port. Connection relations between the first, second and third ports of the optical circulators respectively correspond to connection relations between the first, second and third ports of the 2×2 directional couplers in embodiment 1, embodiment 2, embodiment 3 and embodiment 4.

Corresponding to embodiment 1, the first, second and third ports of the three-port optical circulator respectively correspond to the following ports of the 2×2 directional coupler, which are the port connected with the light source 10, the port connected with the single-mode optical-fiber-input and single-mode optical-fiber-output optical switch 12 and the port connected with the light detection part 14.

Corresponding to embodiment 2, the first, second and third ports of the three-port optical circulator respectively correspond to the following ports of the 2×2 directional coupler, which are the port connected with the beam splitter 15, the port connected with the plurality of optical fibers 13 provided with the label-free optical sensing elements working in the reflection manner 131 on the optical fiber ends and the port connected with the single-mode optical-fiber-input and single-mode optical-fiber-output optical switch 12.

Corresponding to embodiment 3, the first, second and third ports of the three-port optical circulator respectively correspond to the following ports of the 2×2 directional coupler, which are the port connected with the single-mode optical-fiber-input and single-mode optical-fiber-output optical switch 12, the port connected with the plurality of optical fibers 13 provided with the label-free optical sensing elements working in the reflection manner 131 on the optical fiber ends and the port connected with the beam combiner 16.

Embodiment 6

This embodiment provides a multichannel label-free biosensing fiber-optic system, the basic structure of which is as shown in embodiment 1, embodiment 2, embodiment 3, embodiment 4 or/and embodiment 5, wherein the optical fibers in the multichannel label-free biosensing fiber-optic system are replaced by polarization-maintaining optical fibers corresponding to the lightwaves transmitted thereby or a combination of single-mode optical fibers and polarization-maintaining optical fibers.

Embodiment 7

This embodiment provides a multichannel label-free biosensing fiber-optic system, the basic structure of which is as shown in embodiment 1, embodiment 2, embodiment 3, embodiment 4 or/and embodiment 5, wherein the optical fibers in the multichannel label-free biosensing fiber-optic system are replaced by multi-mode optical fibers corresponding to the lightwaves transmitted thereby, or a combination of single-mode optical fibers and multi-mode optical fibers, or a combination of polarization-maintaining optical fibers and multi-mode optical fibers, or a combination of single-mode optical fibers, polarization-maintaining optical fibers and multi-mode optical fibers. A diameter range of the wave guiding fiber cores of the multi-mode optical fibers is 1 μm-10 mm. In one specific embodiment, the diameter range of the wave guiding fiber cores of the multi-mode optical fibers is 1 μm-200 μm. In one specific embodiment, the diameter range of the wave guiding fiber cores of the multi-mode optical fibers is 1 μm-100 μm.

Although using multi-mode optical fibers is disadvantageous in terms of utilizing the optical communication technologies based on single-mode optical fibers or polarization-maintaining optical fibers, beneficial effects such as small size, simple operation and multichannel parallel sensing can still be obtained.

Embodiment 8

This embodiment provides a multichannel label-free biosensing fiber-optic system, the basic structure of which is as shown in embodiment 1, embodiment 2, embodiment 3, embodiment 4, embodiment 5, embodiment 6 or/and embodiment 7, wherein the above-mentioned multichannel label-free biosensing fiber-optic system is used as a basis and other technologies and components are added. For example, 1) a reference channel is added to correct the change of the light source, the light transmission and/or the label-free optical sensing elements working in the reflection manner with time under the influence of factors such as temperature and stress; the reference channel is used for detecting light signals used as a reference, for example, the label-free optical sensing elements working in the reflection manner on the optical fiber ends can be placed in a homogeneous medium such as air or buffer solution, and the reflected signals thereof are measured as a reference, we can either use the optical switch to designate certain time moments when light is incident upon the sensing elements of the reference channel and the reflected light thereof is received by the light detection part, or the reflected light from the label-free optical sensing elements working in the reflection manner of the reference channel is directly received by the light detection part without using the optical switch; the sensing elements on the end facets of the optical fibers in the reference channel can have a gold nano-slit structure, they can also be a non-structured gold film; the reference channel doesn't have to comprise the label-free optical sensing elements working in the reflection manner, for example, the light of the light source can be directly connected to the light detection part through the optical fiber circuit; 2) control or/and change is applied to the polarization of the optical fiber guided waves; and 3) a wavelength-division multiplexing or/and demultiplexing technology is applied to the optical fiber guided waves.

Embodiment 9

Figure 6:
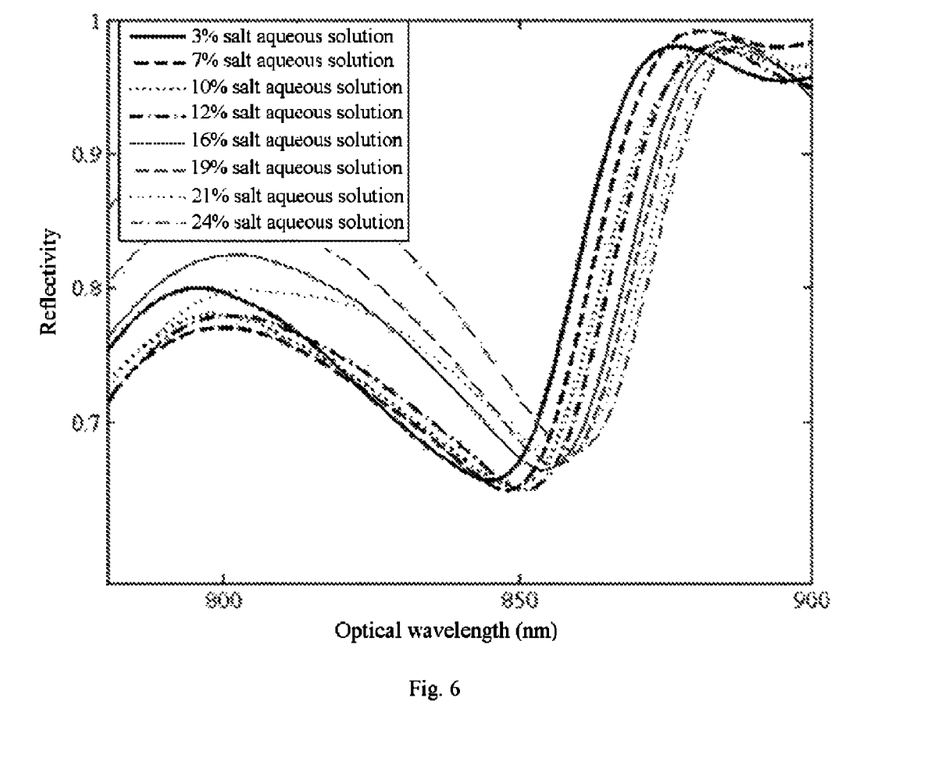
FIG. 6 illustrates a diagram of optical wavelength-reflectivity experimental curves of the multichannel label-free biosensing fiber-optic system according to embodiment 1 of the present invention.

As shown in FIG. 6, in this embodiment, we perform an experiment (optical wavelength-reflectivity experiment) with the multichannel label-free biosensing fiber-optic system of embodiment 1. In this embodiment, the single-mode optical-fiber-input and single-mode optical-fiber-output 1×8 optical switch is switched to a next output port at an interval of 50 ms, and a spectrometer records the reflection spectrum of each channel with an integration time of 40 ms. Eight single-mode optical fibers 13 provided with label-free optical sensing elements working in the reflection manner 131 on the optical fiber end facets are respectively immersed in containers containing salt aqueous solutions of eight different concentrations, which are respectively 3% salt aqueous solution, 7% salt aqueous solution, 10% salt aqueous solution, 12% salt aqueous solution, 16% salt aqueous solution, 19% salt aqueous solution, 21% salt aqueous solution and 24% salt aqueous solution. Finally we obtain eight reflection spectra in parallel, which reveal the different concentrations and optical refractive indices of the eight samples. It can be seen that the multichannel label-free biosensing fiber-optic system provided by the present invention can be used to measure a plurality of samples in parallel, and it also has a quite good stability. In this experiment, we use a broad-band bromine-tungsten halogen lamp as the light source, 2×2 directional couplers with an optical power splitting ratio of 50%:50%, a 1×8 mechanical optical switch, and a mini grating spectrometer as the light detection part. Single-mode optical fibers corresponding to wavelength of 780 nm are used as the optical fibers, and the optical fiber connectors are the FC/APC type. The label-free optical sensing elements working in the reflection manner are gold films which are provided with nano-slit arrays, the thickness of the gold films is 25 nm, the nano-slits penetrate through the entire thickness of the gold films, the period of the nano-slits is 635 nm and the width of the nano-slits is 50 nm.

As described above, the present invention provides a multichannel label-free biosensing fiber-optic system, which comprises one or more light sources coupled into optical fibers, one or more optical fiber circuits for performing coupling or/and directional transmission of optical-fiber guided lightwaves, one or more optical-fiber-input and optical-fiber-output optical switches, a plurality of optical fibers provided with label-free optical sensing elements working in the reflection manner on the optical fiber ends, and the light detection parts, wherein the label-free optical sensing elements working in the reflection manner are attached to the ends of the optical fibers, but not separated from the optical fibers, the label-free optical sensing element working in the reflection manner reflects the optical fiber guided waves, which have come from the light source, passed through the optical fiber circuit and been incident upon it, back to the same optical fiber it is attached to, the reflected light passes through the optical fiber circuit and then is received and measured by the light detection part, the optical-fiber-input and optical-fiber-output optical switch is provided with a plurality of outputs and/or a plurality of inputs, and with the plurality of outputs and/or plurality of inputs, by the switching function, the reflected light from the label-free optical sensing elements working in the reflection manner on the designated optical fiber ends is received by the light detection part, so that multichannel sensing is realized. The present invention provides a label-free biosensing fiber-optic system with parallel multi-channels for detecting a plurality of biological samples. Thanks to utilization of fiber-optic communication technologies such as optical fiber circuit and optical switch, the system can comprise just one light detection part, thereby the complexity of the system is greatly lowered, the size is reduced and the stability is good. Therefore, the present invention effectively overcomes various disadvantages in the prior art and has a great industrial utilization value.

The above-mentioned embodiments are just used for exemplarily describing the principles and effects of the present invention instead of limiting the present invention. One skilled in the art can make modifications or changes to the above-mentioned embodiments without going against the spirit and the range of the present invention. Therefore, all equivalent modifications or changes made by those who have common knowledge in the art without departing from the spirit and technical concept disclosed by the present invention shall be still covered by the claims of the present invention.

What is claimed is:

1. A multichannel label-free biosensing optical fiber system, characterized in that the multichannel label-free biosensing optical fiber system comprises:
   a light source coupled into optical fibers, an optical fiber loop for performing coupling or/and directional transmission to light waves transmitted by the optical fibers, an optical fiber input-output optical switch, a plurality of optical fibers provided with reflective label-free optical sensing elements at ends, and a light detection part, wherein the reflective label-free optical sensing elements are bonded to the ends of the optical fibers, not separated from the optical fibers, the reflective label-free optical sensing elements reflect optical fiber guided waves coming from the light source, passing through the optical fiber loop and then illuminating the optical fibers back to the same optical fibers in which the guided waves are transmitted, reflected light passes through the optical fiber loop and then is received and measured by the light detection part, the optical fiber input-output optical switch is provided with a plurality of loops of outputs and/or inputs, and the reflected light of the reflective label-free optical sensing elements at the ends of designated optical fibers in the plurality of loops of outputs and/or inputs is enabled to be received by the light detection part through the switch to realize multichannel sensing;

the reflective label-free optical sensing elements are gold films which are fabricated on the end surfaces of the optical fibers or/and bonded to the end surfaces of the optical fibers and are provided with nano-trough arrays.

2. The multichannel label-free biosensing optical fiber system according to claim 1, characterized in that the optical fiber loop comprises a directional coupling device, which is used for performing coupling and directional transmission to the light waves transmitted by the optical fibers.

3. The multichannel label-free biosensing optical fiber system according to claim 2, characterized in that the directional coupling device comprises one or a combination of a directional coupler and an optical circulator.

4. The multichannel label-free biosensing optical fiber system according to claim 3, characterized in that the directional coupler is a 2×2 directional coupler with splitting ratio of 50%:50%.

5. The multichannel label-free biosensing optical fiber system according to claim 2, characterized in that a first port of the directional coupling device is connected with the light source, a second port, directly communicated with an input of the first port in a light path, of the directional coupling device is connected with an input end of the optical fiber input-output optical switch, the plurality of optical fibers provided with the reflective label-free optical sensing elements at the ends are connected with output ports of the optical fiber input-output optical switch, and a third port, directly communicated with an input of the second port in the light path, of the directional coupling device is connected with the light detection part.

6. The multichannel label-free biosensing optical fiber system according to claim 2, characterized in that the optical fiber loop further comprises a beam splitter, which is used for performing split beam transmission to the light waves transmitted by the optical fibers.

7. The multichannel label-free biosensing optical fiber system according to claim 6, characterized in that an input port of the beam splitter is connected with the light source, each split beam output port of the beam splitter is connected with a first port of each directional coupling device, the plurality of optical fibers provided with the reflective label-free optical sensing elements at the ends are respectively connected with a second port, directly communicated with an input of the first port in the light path, of each directional coupling device, a plurality of loops of input ports of the optical fiber input-output optical switch are respectively connected with a third port, directly communicated with an input of the second port in the light path, of each directional coupling device, and an output port of the optical fiber input-output optical switch is connected with the light detection part.

8. The multichannel label-free biosensing optical fiber system according to claim 2, characterized in that the optical fiber loop further comprises a beam combiner, which is used for performing combined beam transmission to the light waves transmitted by the plurality of loops of optical fibers.

9. The multichannel label-free biosensing optical fiber system according to claim 8, characterized in that an input port of the optical fiber input-output optical switch is connected with the light source, a plurality of loops of output ports of the optical fiber input-output optical switch are respectively connected with first ports of the directional coupling devices, the plurality of optical fibers provided with the reflective label-free optical sensing elements at the ends are respectively connected with a second port, directly communicated with an input of the first port in the light path, of each directional coupling device, a plurality of loops of input ports of the beam combiner are respectively connected with a third port, directly communicated with an input of the second port in the light path, of each directional coupling device, and an output port of the beam combiner is connected with the light detection part.

10. The multichannel label-free biosensing optical fiber system according to claim 1, characterized in that the multichannel label-free biosensing optical fiber system comprises more than two light sources coupled into optical fibers, or/and more than two optical fiber input-output optical switches, or/and more than two light detection parts, or/and more than two directional coupling devices, or/and more than two beam splitters, or/and more than two beam combiners.

11. The multichannel label-free biosensing optical fiber system according to claims 1, characterized in that the light source comprises one or a combination of a halogen lamp, an optical radiation diode, a super luminescent diode, a super-continuous spectrum light source, an amplified spontaneous emission light source and a laser.

12. The multichannel label-free biosensing optical fiber system according to claims 1, characterized in that the light detection part comprises one or a combination of a spectrometer and an optical power detector.

13. The multichannel label-free biosensing optical fiber system according to claims 1, characterized in that the optical fibers in the multichannel label-free biosensing optical fiber system are single-mode optical fibers corresponding to the light waves transmitted thereby, or polarization-maintaining optical fibers, or a combination of single-mode optical fibers and polarization-maintaining optical fibers.

14. The multichannel label-free biosensing optical fiber system according to claims 1, characterized in that the optical fibers in the multichannel label-free biosensing optical fiber system are multi-mode optical fibers corresponding to the light waves transmitted thereby, or a combination of single-mode optical fibers and multi-mode optical fibers, or a combination of polarization-maintaining optical fibers and multi-mode optical fibers, or a combination of single-mode optical fibers, polarization-maintaining optical fibers and multi-mode optical fibers.

15. The multichannel label-free biosensing optical fiber system according to claim 14, characterized in that a diameter range of wave guiding fiber cores of the multi-mode optical fibers is 1 μm-10 mm.

16. The multichannel label-free biosensing optical fiber system according to claim 15, characterized in that the diameter range of the wave guiding fiber cores of the multi-mode optical fibers is 1 μ-200 μm.

17. The multichannel label-free biosensing optical fiber system according to claim 16, characterized in that the diameter range of the wave guiding fiber cores of the multi-mode optical fibers is 1 μm-100 μm.

18. The multichannel label-free biosensing optical fiber system according to claims 1, characterized in that samples to be detected of the multichannel label-free biosensing optical fiber system are substances that can cause optical refractive index or/and optical path length to change comprising biological molecules, or/and chemical molecules or/and metal ions.

19. The multichannel label-free biosensing optical fiber system according to claim 18, characterized in that the samples to be detected are solution containing molecules to be detected, and when the molecules to be detected are adhered to reflective label-free optical sensing elements, the spectrum or/and intensity of reflected light changes and is measured.

* * * * *